US007098350B2

(12) United States Patent
Dewis et al.

(10) Patent No.: US 7,098,350 B2
(45) Date of Patent: Aug. 29, 2006

(54) E2,E4,Z8-UNDECATRIENOIC ACID AND ESTER AND CARBOXAMIDE DERIVATIVES THEREOF, ORGANOLEPTIC USES THEREOF AND PROCESSES FOR PREPARING SAME

(75) Inventors: Mark L. Dewis, Matawan, NJ (US); Michelle E. Huber, Chadds Ford, PA (US)

(73) Assignee: International Flavors & Fragrances Inc., New York, NY (US)

( * ) Notice: Subject to any disclaimer, the term of this patent is extended or adjusted under 35 U.S.C. 154(b) by 78 days.

(21) Appl. No.: 10/861,751

(22) Filed: Jun. 4, 2004

(65) Prior Publication Data
US 2005/0197387 A1 Sep. 8, 2005

Related U.S. Application Data

(63) Continuation-in-part of application No. 10/618,367, filed on Jul. 10, 2003.

(51) Int. Cl.
C07C 231/00 (2006.01)
(52) U.S. Cl. ............................... 554/69; 54/35; 54/223; 54/224; 54/229; 424/39
(58) Field of Classification Search ................ 554/35, 554/69, 223, 224, 229; 424/39
See application file for complete search history.

(56) References Cited

U.S. PATENT DOCUMENTS

| 3,111,127 A | 11/1963 | Jarboe |
| 4,029,759 A | 6/1977 | Humbert et al. |
| 4,032,661 A | 6/1977 | Rowsell et al. |
| 4,150,052 A | 4/1979 | Watson et al. |
| 4,153,679 A | 5/1979 | Rowsell et al. |
| 4,185,106 A | 1/1980 | Dittmar et al. |
| 4,226,988 A | 10/1980 | Watson et al. |
| 4,296,093 A | 10/1981 | Rowsell et al. |
| 4,470,982 A | 9/1984 | Winkler |
| 4,472,421 A | 9/1984 | Buchel et al. |
| 5,009,893 A | 4/1991 | Cherukuri et al. |
| 5,545,424 A | 8/1996 | Nakatsu et al. |
| 5,624,666 A | 4/1997 | Coffindaffer et al. |
| 5,641,480 A | 6/1997 | Vermeer |
| 5,725,865 A | 3/1998 | Mane et al. |
| 5,730,965 A | 3/1998 | Rapaport |
| 5,843,466 A | 12/1998 | Mane et al. |
| 5,955,066 A | 9/1999 | Sako et al. |
| 6,110,520 A | 8/2000 | He et al. |
| 6,200,554 B1 | 3/2001 | Yeoh et al. |
| 6,210,695 B1 | 4/2001 | Beerse et al. |
| 6,248,315 B1 | 6/2001 | Young et al. |
| 6,251,463 B1 | 6/2001 | Rossy et al. |
| 6,294,186 B1 | 9/2001 | Beerse et al. |
| 6,297,203 B1 | 10/2001 | Guskey et al. |
| 6,299,900 B1 | 10/2001 | Reed et al. |
| 6,303,817 B1 | 10/2001 | Boden et al. |
| 6,328,982 B1 | 12/2001 | Shiroyama et al. |
| 6,333,180 B1 | 12/2001 | Farbood et al. |
| 6,338,855 B1 | 1/2002 | Albacarys et al. |
| 6,365,215 B1 | 4/2002 | Grainger et al. |
| 6,365,601 B1 | 4/2002 | Gaikar et al. |
| 6,391,886 B1 | 5/2002 | Lee |
| 6,451,844 B1 | 9/2002 | Watkins et al. |
| 6,455,080 B1 | 9/2002 | Wolf et al. |
| 6,572,914 B1 | 6/2003 | Borlinghaus |
| 6,579,513 B1 | 6/2003 | Tashjian et al. |
| 6,579,514 B1 | 6/2003 | Hall et al. |
| 6,579,516 B1 | 6/2003 | Mansouri |
| 6,579,535 B1 | 6/2003 | Valentine et al. |
| 6,579,543 B1 | 6/2003 | McClung |
| 2001/0032645 A1 | 10/2001 | Cronk et al. |
| 2002/0012640 A1 | 1/2002 | Mohammadi et al. |
| 2002/0142015 A1 | 10/2002 | Kumamoto et al. |
| 2002/0173436 A1 | 11/2002 | Sonnenberg et al. |
| 2003/0072842 A1 | 4/2003 | Johnson et al. |
| 2003/0082124 A1 | 5/2003 | Hammer |
| 2003/0082129 A1 | 5/2003 | Buckingham et al. |
| 2003/0082271 A1 | 5/2003 | Wolf et al. |
| 2003/0095936 A1 | 5/2003 | Light |
| 2003/0113357 A1 | 6/2003 | Bell et al. |
| 2003/0152682 A1 | 8/2003 | Ley et al. |
| 2004/0241312 A1 | 12/2004 | Gatfield et al. |

FOREIGN PATENT DOCUMENTS

| DE | WO 2004/000787 A2 | 12/2003 |
| EP | 1 121 927 A2 | 2/2001 |
| EP | 1 121 927 A2 | 8/2001 |
| EP | 1 122 233 A1 | 8/2001 |
| GB | 1 438 205 | 3/1976 |
| JP | 04 803546 | 12/1970 |
| JP | 56087505 | 7/1981 |
| WO | WO 93/23005 | 11/1993 |
| WO | WO 98/07404 | 2/1998 |

(Continued)

OTHER PUBLICATIONS

Galophin et al., Abs. of Papers of the 224th ACS National Meeting, Boston, MA, Aug. 18-22, 2002, pp. 139-152.*

(Continued)

*Primary Examiner*—Deborah D. Carr
(74) *Attorney, Agent, or Firm*—Elizabeth M. Quirk

(57) ABSTRACT

Described is a genus of undecatrienoic acid derivatives useful in imparting, augmenting and/or enhancing flavors, aromas and somatosensory effects in or to consumable materials such as foods, beverages, skin care products, oral care products, medicinal products and the like. Also described is a synthesis process for producing such derivatives.

11 Claims, No Drawings

FOREIGN PATENT DOCUMENTS

| WO | WO 99/07235 | 2/1999 |
| WO | WO 00/45815 | 8/2000 |
| WO | WO 02/051392 | 4/2002 |
| WO | WO2004/011415 | 2/2004 |
| WO | WO 2004/043906 | 5/2004 |

OTHER PUBLICATIONS

Chem. Abstr. of Nature, vol. 164, pp. 707-708, 1949, Raphael et al.*
Prior Art Submission Under 37 CFR 1.291.
English abstract of Saureamide In Hochruckextrakten Aus Muntokpfeffer in English. H. Kollmannsberger und S. Nitz, Chem. Mikrobiol. Technol. Lebensm. 14, 87-94 (1992).
"Pellitorine Isomers. II. The Synthesis of N-Isobutyl-trans-2, trans-4-decadienamide[1,2,3]", Martine Jacobson, vol. 75, Jun. 5, 1953, pp. 2584-2586.
"Alkamides from *Artemisia dracunculus*", Bouchra Saadali et al., Phytochemistry, Pergamon Press, vol. 58, No. 7, Dec. 2001, pp. 1083-1086.
"Isobutylamide numbing agents of toothache grass, Ctenium aromaticum" Rubi Gamboa-Leon et al., Biochemical Systematics and ecology, vol. 28, 2000, pp. 1019-1021.
Search for Unsaturated Dienoic Acid Compounds.
GRAS Flavoring Substances 20, Food Technology, vol. 55, No. 12, Dec. 2001 at p. 53.
Rule, et al, Optical Activity and the Polarity of Substituent Groups Part VIII. Growing-chain Effects and the Ortho-Effect in Benzoic Esters, J.Chem.Soc. 1928 (Part I), pp. 1347-1361.
SciFinder (Nov. 20, 2002; Trademark of Chemical Abstracts Service), to wit: malonamic acid, p-menth-3-yl ester, ±-(8Cl) having CAS Registry No. 6129-88-0.
Jaloner, et al, A Molecular Approach to Flavor Synthesis. I. Menthol Esters of Varying Size and Polarity, Journal of Polymer Science:Polymer Chemistry Edition, vol. 18, 2933-2940 (1980).
Ottinger, et al, Systematic Studies on Structure and Physiological Activity of Cyclic Alpha-Keto Enamines, a Novel Class of "Cooling" Compounds, J.Agric.Food Chem., 2001, 49, 5383-5390.
ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin, et al, pp. 139-152.
U.S. Appl. No. 10/411,672, filed Apr. 11, 2003, Dewis et al.
U.S. Appl. No. 10/643,542, filed Aug. 19, 2003, Flammer et al.
"Pungent Alkamides from Spilantes Acmella L. Var. Oleracea Clarke," Nakatani N et al. Bioscience Biotechnology Biochemistry, Japan Soc. For Bioscience Biotechnology and Agrochem., vol. 56, No. 5, 1992, pp. 759-762.
Database Beilstein, Beilstein Institute for Organic Chemistry, J. Chem. Soc., 1952, p. 4338.
"Amides of vegetable origin. VII. Synthesis of N-isobutyldodeca-trans-2, trans-4, trans-8-ans trans-2, trans-4, cis-8-trienamide and the relation to Sanshool I," Crombie L. et al., Journal of Chemical Society, Abstracts, pp. 4244-4249, 1955.
"Isobutylamide numbing agents of toothache grass, Ctenium aromaticum," Rubi Gamboa-Leon et al., Biochemical Systematics and Ecology, 28(10), 2000, pp. 1019-1021.
"Structure and synthesis of a new hypotensive vasodilator isolated from *Spreptomyces aerofaciens*," Tanaka, Hirokazu et al., Tetrahedron Letters 22(35), 1981, pp. 3421-3422.

* cited by examiner

E2,E4,Z8-UNDECATRIENOIC ACID AND ESTER AND CARBOXAMIDE DERIVATIVES THEREOF, ORGANOLEPTIC USES THEREOF AND PROCESSES FOR PREPARING SAME

This is a Continuation-in-Part (CIP) of prior application Ser. No. 10/618,367, filed Jul. 10, 2003.

FIELD OF THE INVENTION

Undecatrienoic acid derivatives, including ester, amide and other derivatives having beneficial flavor and sensory attributes in the oral cavity and on skin.

BACKGROUND OF THE INVENTION

The prior art discloses the presence of $C_{10}$, $C_{11}$ and $C_{12}$ alkatrienoic acids and ester and amide derivatives thereof in a wide variety of botanicals the use thereof to impart flavor and/or a tingling and/or warming sensations in the oral cavity and on skin when used in foodstuffs, chewing gum, oral care products, hair care products, colognes, topical cosmetic products or medicinal products. Such $C_{10}$, $C_{11}$ and $C_{12}$ alkatrienoic acids and ester and amide derivatives thereof are also disclosed as exhibiting biological activity, most notably anti-bacterial, anti-fungal and insecticidal activity. The most significant compounds which are members of the genus: "$C_{10}$, $C_{11}$ and $C_{12}$ alkatrienoic acids and ester and amide derivatives thereof" are those disclosed as follows:

(a) Amides:

Spilanthol or Affinin having the structure

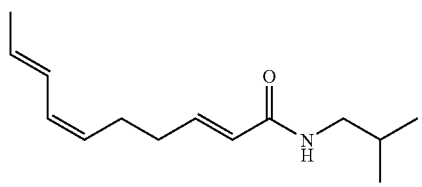

the use of which in oral care, skin care and medicinal products is disclosed in Nakanatsu et al, Published European Patent Application EP 1,121,927 A2; the use of which as an oral sensate, flavor enhancer and potentiator is disclosed in U.S. Published Patent Application 2002/0122778 A1; and the pungency of which is disclosed in Nakatani et al "Pungent Alkamides from *Spilanthes acmella* L. var. *oleracea* Clarke, *Biosci. Biotech. Biochem.*, 56(5), 759–762 (1992);

Isoaffinin having the structure:

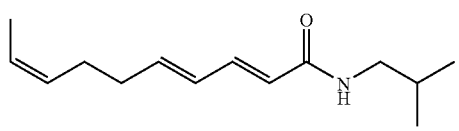

disclosed in Gamboa-Leon et al., "Isobutylamide numbing agents of toothache grass", *Biochemical Systematics and Ecology* 28 (2000) 1019–1021;

N-isobutyl E2, Z7, E9-undecatrienamide having the structure:

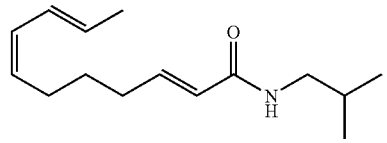

disclosed in Rameswak et al., "Bioactive N-isobutylamides from flower buds of *Spilanthes acmella*", *Phytochemistry* 51 (1999) 729–732;

The disclosure of the compound having the structure:

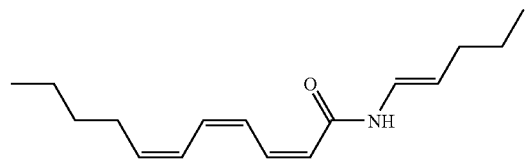

by Snider et al., "Synthesis of the N-((1E)-Alkenyl)-(2Z, 4Z)-heptadienamide Side Clain of Salicilihalamide A and Apicularens A and B", *Organic Letters* (2000), Vol. 2, No. 3, pp. 407–408.

(b) Acids:

The presence of dodecatrienoic acid (structure not specified) in a Hop Plant named "YCR Accession No. 14" having an aroma with sharp, floral and spicy notes, as disclosed in Zimmermann, U.S. Plant Patent PP12,213 P2;

The disclosure of the compound having the structure:

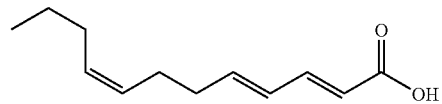

by Crombie, "*Amides of Vegetable Origin, Part VII, Synthesis of N-isobutyldodeca-trans-2:trans-4:trans-8- and trans-2:trans-4:cis-8-trienamide and their relation to Sanshool I*", J. Chem. Soc. 1955, pp. 4244–4249.

Published application for U.S. Patent 2003/0068330 A1 published on Apr. 10, 2003 discloses 2,6,10-dodecatrienoic acid (without specifying any particular isomer thereof) for potentiating the activity of Nerve Growth Factor (NGF).

(c) Esters:

The disclosure of the compound having the structure:

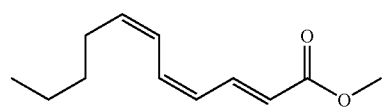

by Furber et al., "Stereospecific Diene Synthesis using Acetylene Carbocupration; Preparation of Navel Orangeworm Pheremone and Leukotriene Analogues", *J. Chem. Soc. Perkin Trans. I*, 1986, pp. 1809–1815;

The disclosure of the compound having the structure:

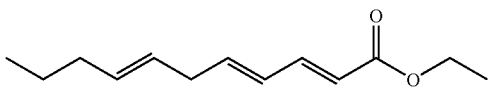

by Tanaka et al., "Structure and Synthesis of a New Hypotensive Vasodilator Isolated from *Streptomyces Aureofaciens*", *Tetrahedron Letters*, Vol. 22, No. 35, pp. 3421–3422, 1981.

Despite the existence in the prior art and in commerce of such a vast number of $C_{10}$, $C_{11}$ and $C_{12}$ alkatrienoic acids and ester and amide derivatives thereof, there is an increasing ongoing need for flavor ingredients, skin care ingredients, oral care ingredients and hair care ingredients that exhibit organoleptically-acceptable somatosensory activity or flavor property, particularly at relatively low threshold levels.

SUMMARY OF THE INVENTION

The present invention relates to novel compounds of the structure:

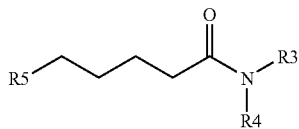

where $R^3$ is selected from the group consisting of hydrogen, methyl and ethyl;

$R^4$ is selected from the group consisting of methyl, ethyl, n-propyl, cyclopropyl, isopropyl, n-butyl, sec-butyl, isobutyl, 2-methyl butyl, cyclobutyl,

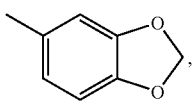

cylcopentyl, allyl, methallyl, $CH_2CH(OH)CH_3$, $CH(CH_3)CH_2OH$, $CH_2C(CH_3)OH$, $CH_2CH_2OH$, $CH_2CO_2CH_3$, geranyl, neryl or where $R^3$ and $R^4$ together form the structures:

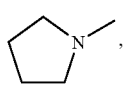 , 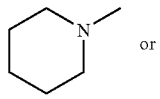 or 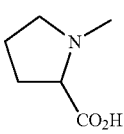

and $R^5$ is selected from the group consisting of $CH_2CH=CHCH_2CH_3$ (z); $CH_2CH=CHCH_2CH_2CH_3$ (z); $CH_2CH=CHCH_2CH_2CH_2CH_3$(z); $CH_2CH_2CH=CHCH_3$(z); $CH_2CH_2CH=CHCH_3$(z); $CH_2CH_2CH=CHCH_2CH_3$ (z); $CH_2CH_2CH=CHCH_2CH_2CH_3$(z); $CH_2CH_2CH_2CH=CHCH_3$(z); $CH_2CH_2CH_2CH=CHCH_2CH_3$(z) and;

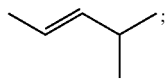

as well as the compounds

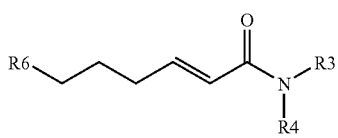

where $R^3$ and $R^4$ are as described above; and $R^6$ is selected from the group consisting of:
$CH_2CH_2CH=CHCH_2CH_3$(z);
$CH_2CH_2CH=CHCH_2CH_3$(z);
$CH_2CH=CHCH_2CH_3$(z);
$CH_2CH=CHCH_3$(z); and
$CH_2CH=CHCH_2CH_2CH_3$(z).

Our invention relates to novel compounds which are members of the genus: undecatrienoic acid derivatives thereof and a process for augmenting, enhancing or imparting an aroma or taste or somatosensory effect in or to a consumable material which is, in the alternative, a foodstuff, a beverage, a chewing gum, an oral care product, a nasal care product, a cologne, a skin care product, a hair care product, a topical cosmetic product or a medicinal product comprising the step of adding to said consumable material a taste or aroma or somatosensory effect-augmenting, enhancing or imparting quantity and concentration of at least one undecatrienoic acid derivative of the structures set forth above.

In another embodiment, the present invention is directed to the use of the compound as described in the applications set forth herein, The compound is defined according to the structure:

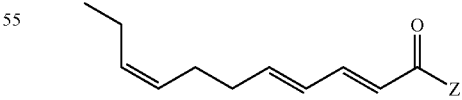

wherein Z represents —$OR^2$ or —$NRR^1$ with the provisos that when Z is —$OR^2$, $R^2$ is hydrogen, $C_1$–$C_6$ straight chain or branched-chain alkyl or $C_3$–$C_6$ straight chain or branched-chain alkenyl; and when Z is —$NRR^1$, R represents, in the alternative, hydrogen, methyl or ethyl and $R^1$ represents methyl, ethyl, n-propyl, cyclopropyl, isopropyl, n-butyl, sec-butyl, isobutyl, 2-methylbutyl, cyclobutyl,

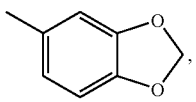

cyclopentyl or allyl.

More specifically, and more preferably, our invention is directed to augmenting or imparting a flavor or somatosensory effect to a foodstuff, chewing gum, medicinal product, toothpaste, alcoholic beverage, aqueous beverage, dairy product, confection, chocolate, sweet composition or savory composition comprising the step of adding to foodstuff, chewing gum, medicinal product, toothpaste, alcoholic beverage, aqueous beverage, dairy product, confection, chocolate, sweet composition or savory composition a flavor or sensation augmenting, enhancing or imparting quantity and concentration of at least one E2,E4,Z8-undecatrienoic acid derivative defined according to the structure:

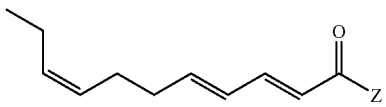

wherein the moiety Z is defined herein.

As used herein the compounds of our invention having the structure:

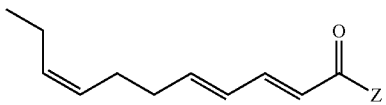

will be referred hereinafter to as "2,4,8-undecatrienoic acid derivatives".

Our invention is also directed to a synthesis process for preparing the 2,4,8-undecatrienoic acid derivatives of our invention by means of first oxidizing the E2, E4, Z8-undecatrienal with silver(I)oxide in aqueous alkali metal hydroxide media followed by acidifcation in order to form the E2, E4, Z8-undecatrienoic acid, which may be utilized as such for its organoleptic and/or somatosensory properties in consumable materials; or which may be further reacted with an alkyl haloformate in admixture with a tertiary amine base in order to form an intermediate which, in turn is reacted with either (a) an amine having the formula $RR^1NH$ in order to form a member of the E2, E4, Z8-undecatrienoic acid amide subgenus of our invention or (b) an alcohol having the formula $R^2OH$ in order to form a member of the E2, E4, Z8-undecatrienoic acid ester subgenus of our invention.

DETAILED DESCRIPTION OF THE INVENTION

Our invention specifically relates to the compositions described above and uses thereof preferably in augmenting or imparting an olfactory effect, flavor or a sensation such as a taste or somatosensory effect to a foodstuff, chewing gum, medicinal product, toothpaste, alcoholic beverage, aqueous beverage, dairy product, confection, chocolate, sweet composition or savory composition particularly providing (a) flavor; (b) tingle sensation; (c) warming/burning sensation; (d) numbing sensation; (e) umami taste and (f) salt enhancing effects.

Specific members of the compounds are 2,4,8-undecatrienoic acid derivatives which are members of the genus having the structure:

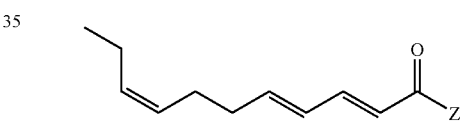

wherein the moiety Z is defined herein.

Specific members of the 2,4,8-undecatrienoic acid derivative genus of our invention have organoleptic and somatosensory properties as set forth in the following Table I:

TABLE I

| Z | R | $R^1$ | $R^2$ | Compound | Primary Flavor or Sensory Characteristic |
|---|---|---|---|---|---|
| —$NRR^1$ | H | isobutyl | N/A | N-isobutyl E2,E4,Z8-undecatrienamide | Strong tingle at 10 ppm. Green, cucumber and melon flavor with pleasant seashore aroma. |
| —$NRR^1$ | methyl | methyl | N/A | N,N-dimethyl E2,E4,Z8-undecatrienamide | At 1 ppm, a flaxseed oil, cod liver oil taste with light tingle and pleasant seashore aroma nuances. |
| —$OR^2$ | N/A | N/A | H | E2,E4,Z8-undecatrienoic acid | At 1 ppm in water, a cod liver oil taste with green, fatty nuances. |
| —$OR^2$ | N/A | N/A | —$CH_3$ | Methyl E2,E4,Z8-undecatrienoate | At 1 ppm, a pleasant seashore aroma, and a sardine-like taste having a fruity topnote and an aesthetically pleasing astringent effect. |

Other compounds of the present invention include n-isobutyl Z7-decenamide, n-cyclopropyl Z7-decenamide, n-ethyl-E2, Z8-undecadienamide, n-cyclopropyl-E2, Z8-undacadienamide, n-isobutyl-E2,Z8-undecadeineamide, n-isobutyl-E2,Z8-undecadienamide, n-isobutyl-E2,Z9-dodecadienamide and N-(3,4-mentylenedioxy)benzyl-8-methyl-6-noneamide.

The following Table II sets forth examples of processes and compositions where the 2,4,8-undecatrienoic acid derivatives of our invention are utilized. Each of the useful ingredients set forth in the cited references, including the examples thereof is usable in the practice of our invention:

TABLE II

| Nature of Use of the Undecatrienoic Acid Derivatives of our Invention | Reference Containing Examples Where the Undecatrienoic Acid Derivative of our Invention are Utilizable |
| --- | --- |
| Skin care | U.S. Pat. No. 6,096,324 |
| Cosmetics, toiletries and bath agents | U.S. Pat. No. 6,328,982 |
| Skin care, cosmetic and hair care compositions | U.S. Pat. No. 6,544,499 |
| Nasal cavity care compositions | U.S. Pat. No. 6,576,224 |
| Dental care compositions | U.S. Pat. No. 6,576,225 |
| Personal wash sunscreen compositions | U.S. Pat. No. 6,576,228 |
| Hair Care Compositions | U.S. Patent Application 2001/0043912 A1 published on Nov. 22, 2001 |
| Skin care compositions | U.S. Patent Application 2002/0039591 A1 |
| Oral sensates, flavor enhancers and potentiators | U.S. Patent Application 2002/0122778 A1 |
| Hair care compositions | U.S. Patent Application 2003/0035784 A1 |
| Hair and scalp care compositions | U.S. Patent Application 2003/0095938 A1 |
| Food, pharmaceutical and personal care products | European Application EP 1,121,927 A2 published Aug. 8, 2001 |
| Anti-dandruff and anti-itch compositions | U.S. Patent Application 10/067,596 filed on Feb. 5, 2002 |
| Taste and sensory effect compositions | U.S. Patent Application 10/411,672 filed on Apr. 11, 2003 |

As used herein olfactory effective amount is understood to mean the amount of compound in flavor compositions, oral care compositions, nasal care compositions, skin care compositions, hair and scalp care compositions, cosmetic compositions and other consumable materials as defined supra, the individual component will contribute to its particular olfactory characteristics, but the flavor, taste and aroma effect on the overall composition will be the sum of the effects of each of the flavor ingredients. As used herein taste effects include salt and umami effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of undecatrienoic acid derivatives used in products is greater than 10 parts per billion, generally provided at a level of from about 50 parts per billion to about 200 parts per million in the finished product, more preferably from about 100 parts per billion to about 100 parts per million by weight.

The usage level of undecatrienoic acid derivatives varies depending on the product in which the undecatrienoic acid derivatives are employed. For example, alcoholic beverages the usage level is from about 0.5 to about 25 parts per million, preferably from about 2 to about 10 and most preferably from about 5 to about 10 parts per million by weight. Non-alcoholic beverages are flavored at levels of from about 25 parts per billion to about 2 parts per million, preferably from about 100 parts per billion to about 0.5 parts per million and in highly preferred situations of from about 150 to about 400 parts per billion. Snack foods can be advantageously flavored using undecatrienoic acid derivatives of the present invention at levels of from about 5 to about 250 parts per million, preferably from about 25 to about 200 and most preferably from about 35 to about 75 parts per million by weight.

The usage level of undecatrienoic acid derivative compounds varies depending on the product in which the undecatrienoic acid derivative compounds are employed. For example, alcoholic beverages the usage level is from about 1 to about 50 parts per million, preferably from about 5 to about 30 and most preferably from about 10 to about 25 parts per million by weight. Non-alcoholic beverages are flavored at levels of from about 50 parts per billion to about 5 parts per million, preferably from about 200 parts per billion to about 1 part per million and in highly preferred situations of from about 300 to about 800 parts per billion. Snack foods can be advantageously flavored using undecatrienoic acid derivative compounds of the present invention at levels of from about 10 to about 250 parts per million, preferably from about 50 to about 200 and most preferably from about 75 to about 150 parts per million by weight.

Toothpaste can be satisfactorily flavored by using undecatrienoic acid derivative compounds at levels of from about 150 to about 500 parts per million, more preferably from about 200 to about 400 parts per million by weight.

Candy products including hard candy can be flavored at levels of from about 10 to about 200; preferably from about 25 to about 150 and more preferably from 50 to 100 parts per million by weight. Gum usage levels are from about 300 to about 800, preferably from about 450 to about 600 parts per million.

The present invention also provides a method for enhancing or modifying the salt flavor of a food through the incorporation of an organoleptically acceptable level of the compounds described herein. The compounds can be used individually or in combination with other salt enhancing compounds of the present invention. In addition, the salt enhancing materials of the present invention can be used in combination with other salt enhancing compositions known in the art, including but not limited to cetylpyridium chloride, bretylium tosylate, various polypeptides, mixtures of calcium salts of ascorbic acid, sodium chloride and potassium chloride, as described in various U.S. Pat. Nos. 4,997, 672; 5,288,510; 6,541,050 and U.S. Patent Application 2003/0091721.

The salt taste enhancing compounds of the present invention may be employed to enhance the perceived salt taste of any salts used in food or beverage products. The preferred salt taste to be enhanced by the compounds of the present invention is that of sodium chloride, primarily because of the discovery that ingestion of large amounts of sodium may have adverse effects on humans and the resultant desirability of reducing salt content while retaining salt taste.

In addition, the compounds of the present invention may also be employed to enhance the perceived salt taste of known salty tasting compounds which may be used as salt substitutes. Such compounds include cationic amino acids and low molecular weight dipeptides. Specific examples of these compounds are arginine, hydrochloride, lysine hydrochloride and lysine-ornithine hydrochloride. These compounds exhibit a salty taste but are typically useful only at low concentrations since they exhibit a bitter flavor at higher concentrations. Thus, it is feasible to reduce the sodium chloride content of a food or beverage product by first formulating a food or beverage with less sodium chloride than is necessary to achieve a desired salt taste and then adding to said food or beverage the compounds of the present invention in an amount sufficient to potentiate the salt taste of said salted food or beverage to reach said desired taste. In addition, the sodium chloride content may be further reduced by substituting a salty-tasting cationic amino acid, a low molecular weight dipeptide or mixtures thereof for at least a portion of the salt.

The salt enhancing level of the compounds of the present invention range from about 100 parts per billion to about 100 parts per million; preferably from about 0.1 parts per million to about 50 parts per million; and most preferably from about 0.5 parts per million to about 10 parts per million when incorporated into the foodstuff.

The term "foodstuff" as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the undecatrienoic acid derivative compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the undecatrienoic acid derivatives of our invention; (2) that they be organoleptically compatible with the undecatrienoic acid derivatives of our invention whereby the flavor of the ultimate consumable material to which the undecatrienoic acid derivatives are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the undecatrienoic acid derivatives of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillyl butyl ether, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimeth-oxyphenol; amyl acetate; amyl cinnamate; γ-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guaiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

The undecatrienoic acid derivatives of our invention or compositions incorporating them, as mentioned above, can be combined with one or more vehicles or carriers for adding them to the particular product. Vehicles can be water-soluble or oil-soluble edible or otherwise suitable materials such as triacetin, vegetable oil, triethyl citrate, ethyl alcohol, propylene glycol, water and the like. Carriers include materials such as gum arabic, carrageenan, xanthan gum, guar gum and the like.

The undecatrienoic acid derivatives prepared according to our invention can be incorporated with the carriers by conventional means such as spray-drying, extrusion, drum-drying and the like. Such carriers can also include materials for coacervating the undecatrienoic acid derivatives of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of undecatrienoic acid derivatives utilized should be sufficient to impart the desired flavor characteristic to the product, but on the other hand, the use of an excessive amount of undecatrienoic acid derivatives is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology effective amount and sufficient amount is understood in the context of the present invention to be quantitatively adequate to alter the flavor of the foodstuff.

With reference to the novel compounds of our invention, the synthesis is effected by means of the oxidation of E2,E4,Z8-undecatrienal with silver (I) oxide in sodium hydroxide solution. Acidification liberates the E2,E4,Z8-undecatrienoic acid. Subsequent reaction with ethyl chloroformate in the presence of triethylamine and further reaction of the intermediate with amine or alcohol (added either directly or in solution) according to the scheme:

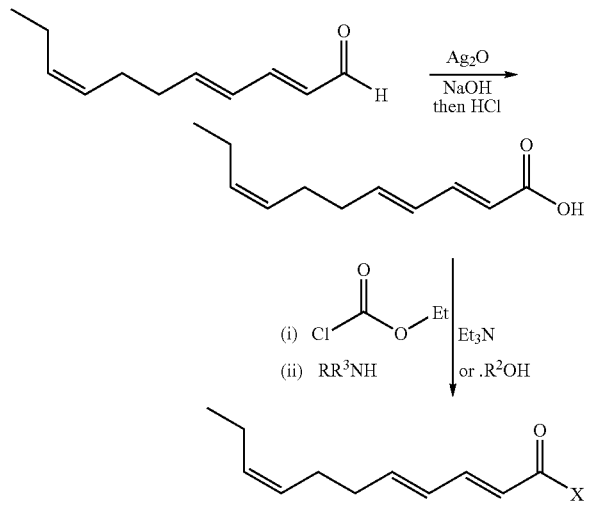

wherein X represents —OR$^2$ or —NRR$^1$ as set forth in the examples herein and wherein when X is —OR$^2$, R$^2$ is C$_1$–C$_6$ straight chain or branched-chain alkyl or C$_3$–C$_6$ straight chain or branched-chain alkenyl; and when X is —NRR$^1$, R represents, in the alternative, hydrogen, methyl or ethyl and R$^1$ represents methyl, ethyl, n-propyl, cyclopropyl, isopropyl, n-butyl, sec-butyl, isobutyl, 2-methylbutyl, cyclobutyl,

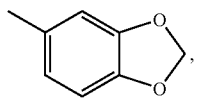

cyclopentyl or allyl.

For example, the 2,4,8-undecatrienal is added to a suspension of silver (I) oxide (1.1 eq) in water. The mixture is stirred at 20° C. and 50% sodium hydroxide solution (equal weight to the aldehyde), is added over 30 minutes allowing the batch to exotherm to 60° C. The solution is filtered through celite, and the aqueous filtrate acidified to pH 1 with hydrochloric acid solution, to give 2,4,8-undecatrienoic acid.

The 2,4,8-undecatrienoic acid may be isolated and utilized for its organoleptic properties, or it may be dissolved in an solvent such as n-hexane, toluene, chloroform, tetrahydrofuran (THF) or dichloromethane to which an alkyl haloformate, preferably ethylchloroformate is added in 1.0 to 2.0 equivalents at temperature ranging from 0° C. to room temperature, most preferably from 10° C. to 20° C. The resulting solution is cooled to −10° C. to −30° C., and an aromatic or aliphatic tertiary amine such as pyridine, 4(N, N-dimethylamino)pyridine or triethylamine is added in 1.0 to 2.0 equivalents such that the temperature range is below 0° C. and the mixture aged for 1 hour. The mixture is filtered, and the filtrate cooled to 0° C. At this point an intermediate having, for example the structure:

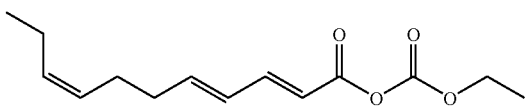

is formed, when the alkyl haloformate is ethyl chloroformate.

For Amides:

The amine is added in 1.0 to 7.0 equivalents either neat or as a solution in THF and the reaction is aged for about 1–3 hours at room temperature. The reaction is quenched with 10% aqueous hydrochloric acid, washed with 10% sodium hydroxide followed by sodium chloride solution, and the solvent removed.

The crude product is purified by distillation or recrystallization depending on the physical properties. The reaction occurs in 40–80% mole yield based on 2,4,8-undecatrienoic acid.

For Esters:

An alcohol of the formula R$^2$OH, e.g., ethyl alcohol (10 eq) is added and the reaction is stirred overnight at room temperature. The reaction is quenched with 10% aqueous hydrochloric acid, washed 5% sodium hydroxide solution and finally with water and the solvent is removed.

The crude product is purified by distillation and the reaction occurs in 60–85% mole yield based on 2,4,8-undecatrienoic acid.

The 2,4,8-undecatrienoic acid derivatives of the present invention can be admixed with other flavoring agents and incorporated into foodstuffs and other products using techniques well known to those with ordinary skill in the art. Most commonly the 2,4,8-undecatrienoic acid derivatives are simply admixed using the desired ingredients within the proportions stated.

The following examples are provided as specific embodiments of the present invention. Other modifications of this invention will be readily apparent to those skilled in the art, without departing from the scope of this invention. As used herein, both the specification and the following examples all percentages are weight percent unless noted to the contrary.

EXAMPLE 1

Preparation of Materials of the Present Invention

The following reaction sequence was used to prepare the specific compounds described by the NMR data set forth below:

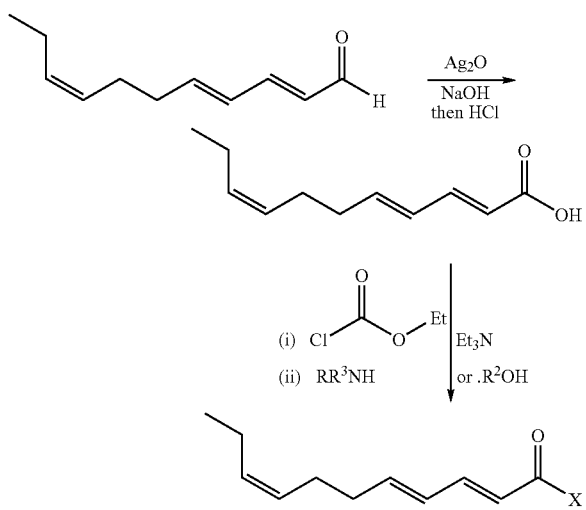

2,4,8-Undecatrienal was added to a suspension of silver (I) oxide (1.1 eq) in water. The mixture was stirred at 20° C. and concentrated sodium hydroxide solution (equal weight to the aldehyde), was added over 30 minutes allowing the batch to exotherm to 60° C. The solution was filtered through celite, and the aqueous filtrate acidified to pH 1 with hydrochloric acid solution, to give 2,4,8-undecatrienoic acid.

2,4,8-undecatrienoic acid was dissolved in dichloromethane to which ethylchloroformate was added in 1.0 to 2.0 equivalents at a temperature ranging from 0° C. to room temperature, most preferably from 10° C. to 20° C. The resulting solution was cooled to −10° C. to −30° C., and triethylamine was added in 1.0 to 2.0 equivalents such that the temperature range was below 0° C. and the mixture aged for 1 hour. The mixture was filtered, and the filtrate cooled to 0° C.

For Amides:

The amine was added in 1.0 to 7.0 equivalents either neat or as a solution in THF and the reaction was aged for about 1–3 hours at room temperature. The reaction was quenched with 10% aqueous hydrochloric acid, washed with 10% sodium hydroxide followed by sodium chloride solution, and the solvent removed.

The crude product was purified by distillation or recrystallization depending on the physical properties. The reaction occurred in 40–80% mole yield based on 2,4,8-undecatrienoic acid.

For Esters:

Alcohol (10 eq) was added and the reaction was stirred overnight at room temperature. The reaction was quenched with 10% aqueous hydrochloric acid, washed with 5% sodium hydroxide solution and finally with water and the solvent was removed.

The crude product was purified by distillation and the reaction occurred in 60–85% mole yield based on 2,4,8-undecatrienoic acid.

The amides and esters were synthesized according to the general scheme above with the following specific examples. Equivalents set out were mole equivalents based on starting acid, yields were purified chemical yields based on starting acid.

The following examples 1(A)–1(D) set forth syntheses of specific 2,4,8-undecatrienoic acid derivatives of our invention and include NMR data.

EXAMPLE 1(A)

E2,E4,Z8-undecatrienoic Acid

E2,E4,Z8-undecatrienal 1 eq, silver (I) oxide 1.1 eq, concentrated sodium hydroxide solution 1 weight eq, acidified to pH1 with conc. hydrogen chloride solution, yield=43%.

| | |
|---|---|
| 0.96 ppm | (t, 3H, J = 7.53 Hz) |
| 2.04 ppm | (quintet, 2H, J = 7.41 Hz) |
| 2.19 ppm | (t, 2H, J = 6.27 Hz) |
| 2.24 ppm | (t, 2H, J = 6.23 Hz) |
| 5.32 ppm | (m, 1H) |
| 5.40 ppm | (m, 1H) |
| 5.79 ppm | (d, 1H, J = 15.35 Hz) |
| 6.20 ppm | (m, 2H) |
| 7.34 ppm | (d, 1H, J = 15.34 Hz, of d, J = 10.12 Hz) |

EXAMPLE 1(B)

N-isobutyl E2,E4,Z8-undecatrienamide

E2,E4,Z8-undecatrienoic acid 1 eq, ethyl chloroformate 1.5 eq, triethylamine 1.5 eq, isobutylamine 1.2 eq, quench as per general procedure, yield=75%.

| | |
|---|---|
| 0.93 ppm | (d, 6H, J = 6.64 Hz) |
| 0.95 ppm | (t, 3H, J = 7.52 Hz) |
| 1.80 ppm | (septet, 1H, J = 6.73 Hz) |
| 2.03 ppm | (quintet, 2H, J = 7.40 Hz) |
| 2.19 ppm | (m, 4H) |
| 3.17 ppm | (t, 2H, J = 6.48 Hz) |
| 5.16–5.37 ppm | (m, 2H) |
| 5.39 ppm | (br. s, 1H) |
| 5.76 ppm | (d, 1H, J = 15.01 Hz) |
| 6.02–6.19 ppm | (m, 2H, j) |
| 7.19 ppm | (d, 1H, J = 14.96 Hz, of d, J = 10.24 Hz) |

EXAMPLE 1(C)

N,N-dimethyl E2,E4,Z8-undecatrienamide

E2,E4,Z8-undecatrienoic acid 1 eq, ethyl chloroformate 1.5 eq, triethylamine 1.5 eq, dimethylamine (2.0M solution in THF) 3.0 eq, quench as per general procedure, yield=67%.

| | |
|---|---|
| 0.95 ppm | (t, 3H, J = 7.54 Hz) |
| 1.25 ppm | (t, 3H, J = 7.10 Hz) |
| 2.03 ppm | (quintet, 2H, J = 7.39 Hz) |
| 2.19 ppm | (m, 4H) |
| 2.90 ppm | (s) |
| 3.01 ppm | (s, 3H) |
| 3.07 ppm | (s, 3H) |
| 4.11 ppm | (q, 2H, J = 7.12 Hz) |
| 5.28–5.43 ppm | (m, 2H) |
| 6.02–6.10 ppm | (m, 1H) |
| 6.17–6.25 ppm | (m, 1H) |
| 6.26 ppm | (d, 1H, J = 14.79 Hz) |
| 7.23 ppm | (d, 1H, J = 14.76 Hz, of d, J=10.26 Hz) |

EXAMPLE 1(D)

Methyl E2,E4,Z8-undecatrienoate

E2,E4,Z8-undecatrienoic acid 1 eq, ethyl chloroformate 1.5 eq, triethylamine 1.5 eq, methanol 10.0 eq, quench as per general procedure, yield=83%.

| | |
|---|---|
| 0.95 ppm | (t, 3H, J=7.53 Hz) |
| 1.25 ppm | (t, 3H, J=7.15 Hz) |
| 2.04 ppm | (quintet, 2H, J=7.67 Hz) |
| 2.22 ppm | (m, 4H) |
| 3.73 ppm | (s, 3H) |
| 4.12 ppm | (q, 2H, J=7.14 Hz) |
| 5.26–5.46 ppm | (m, 2H) |
| 5.80 ppm | (d, 1H, J=15.45 Hz) |
| 6.08–6.23 ppm | (m, 2H) |
| 7.26 ppm | (d, 1H, J=15.39 Hz, of d, J=9.97 Hz) |

EXAMPLE 2

Preparation of an Alcoholic Beverage

The following formulation was prepared:

| Ingredients | Volume |
|---|---|
| 190° Proof food grade Ethyl Alcohol | 157.89 mL |
| High Fructose Corn Syrup 55 (77° Brix) | 217.00 mL |
| Citric Acid (50% solution) | 3.00 mL |
| Water | 622.11 mL |

Flavored beverages were prepared using the above 30° proof alcoholic base. A kiwi flavor was applied to the beverages. This flavor consisted of cis-3 hexenol, trans-2 hexenal, ethyl butyrate, ethyl-2-methyl butyrate, isoamyl butyrate, ethyl acetate, ethyl isovalerate, and trans-2-hexenol in equal proportions. The control beverage contained 200 ppm of the above flavor blend. This control beverage exhibited the taste characteristics of a candied kiwi flavor with moderate apple character. Another beverage was prepared containing 200 ppm of the same flavor and 3 ppm of N-isobutyl E2,E4,Z8-undecatrienamide prepared according to Example 1(B). The flavor of this beverage was slightly more melon rind in character than the control. There was also an enhanced perception of alcohol and a tingle effect on the tongue.

EXAMPLE 3

Preparation of Hard Candy

The following formulation was prepared:

| Ingredients | Parts by Weight |
|---|---|
| Sucrose | 137 grams |
| Corn Syrup 42 DE | 91 grams |
| Water | 46 grams |

The above formulation was added to a stainless steel pot. With constant mixing, the formulation temperature was raised to 295° F. The pot was then removed from the heat, and 1.0 grams of a cola flavor containing the ingredients in equal amounts: cinnamic aldehyde, ginger oil, lemon oil, lime oil and nutmeg oil was added and blended with the sucrose-corn syrup-water formulation. After the blending was complete, 1.2 grams of citric acid was added. The resulting liquid candy was then deposited into molds, and the molds containing the liquid candy were cooled to room temperature, yielding 200 grams of finished hard candy. The resulting control candy exhibited a typical cola flavor having citrus and spice taste and aroma nuances. A second candy sample was prepared using the above recipe modified by the addition of 50 ppm of N-isobutyl E2, E4, Z8-undecatrienamide prepared according the procedure of Example 1 (B). This second candy sample exhibited a moderately strong and substantive cola profile, as well as a taste effect similar to carbonation.

EXAMPLE 4

Additional Compounds

The following compounds were made by reacting the recited reagents using the reaction sequences set descrbied above and using the equipment set forth in the examples. After the compounds were isolated and the yields obtained, the NMR data was obtained:

N-Cyclopropyl 2E,8Z-undecadienamide 2E,8Z-Undecadienoic acid 1 eq, ethyl chloroformate 1.2 eq, triethylamine 1.3 eq, cyclopropylamine 1.3 eq as a 2.0 M solution in THF, quench as per general procedure, yield=57%.

0.50–0.53 ppm (m, 2H), 0.80 ppm (m, 2H), 0.95 ppm (t, 3H, J=7.52 Hz), 1.33–1.48 (m, 4H), 2.03 ppm (m, 4H), 2.16 ppm (q, 2H, J=7.14 Hz), 2.78 ppm (m, 1H), 5.30 ppm (m, 1H), 5.36 ppm (m, 1H), 5.50 ppm (br. s, 1H), 5.69 ppm (d, 1H, J=15.28 Hz), 6.82 ppm (d, 1H, J=15.25 Hz, of t, J=6.95 Hz).

N-Ethyl 2E,8Z-undecadienamide 2E,8Z-Undecadienoic acid 1 eq, ethyl chloroformate 1.5 eq, triethylamine 1.6 eq, ethylamine 1.6 eq as a 2.0M solution in THF, quench as per general procedure, yield=64%.

0.95 ppm (t, 3H, J=7.56 Hz), 1.16 ppm (t, 3H, J=7.27 Hz), 1.35–1.48 ppm (m, 4H), 2.00–2.05 ppm (m, 4H), 2.14–2.19 ppm (m, 2H), 3.34 ppm (pentet, 1H, J=7.23 Hz), 5.28–5.39 ppm (m, 2H), 5.81 ppm (d, 1H, J=15.27 Hz, of d, J=1.38 Hz), 6.08 ppm (br. s, 1H), 6.80 ppm (d, 1H, J=15.28 Hz, of t, J=7.06 Hz).

N-(3,4-methylenedioxy)benzyl E2, Z6-nonadienamide 2E,6Z-Nonadienoic acid 1 eq, ethyl chloroformate 1.5 eq, triethylamine 1.6 eq, (3,4-methylenedioxy)benzylamine 2.0 eq, quench as per general procedure, yield=44%. 0.95 ppm (t, 3H, J=7.53 Hz), 2.03 ppm (pentet, 2H, J=7.37 Hz), 2.17–2.23 ppm (m, 4H), 4.39 ppm (d, 2H, J=5.64 Hz), 5.29–5.42 ppm (m, 2H), 5.76 ppm (br.s, 1H), 5.78 ppm (d, 1H, J=15.38 Hz), 5.94 ppm (s, 2H), 6.75–6.79 ppm (m, 3H), 6.86 ppm (d, 1H, J=15.27 Hz, of t, J=6.59 Hz).

All U.S. Patents and Published Patent Applications as set forth in the specification are herein incorporated by reference.

What is claimed is:

1. The compound having the structure:

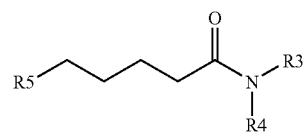

where R³ is selected from the group consisting of hydrogen, methyl and ethyl;

R⁴ is selected from the group consisting of methyl, ethyl, n-propyl, cyclopropyl, isopropyl, n-butyl, sec-butyl, isobutyl, 2-methyl butyl, cyclobutyl,

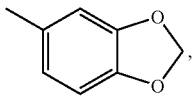

cylcopentyl, allyl, methallyl, CH₂CH(OH)CH₃, CH(CH₃)CH₂OH, CH₂C(CH₃)OH, CH₂CH₂OH, CH₂CO₂CH₃, geranyl, neryl or where R³ and R⁴ together form the structures:

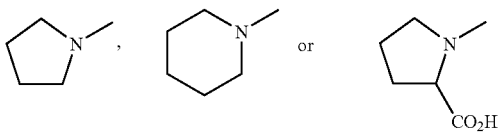

and R⁵ is selected from the group consisting of CH₂CH═CHCH₂CH₃ (z); CH₂CH═CHCH₂CH₂CH₃ (z); CH₂CH═CHCH₂CH₂CH₂CH₃(z); CH₂CH₂CH═CHCH₃(z); CH₂CH₂CH═CHCH₃(z); CH₂CH₂CH═CHCH₂CH₃(z); CH₂CH₂CH═CHCH₂CH₃(z); CH₂CH₂CH₂CH═CHCH₃(z); CH₂CH₂CH₂CH═CHCH₂CH₃(z) and;

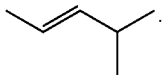

2. The compound having the structure:

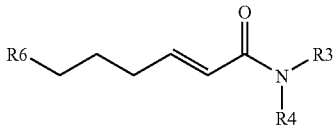

where R³ is selected from the group consisting of hydrogen, methyl and ethyl;

R⁴ is selected from the group consisting of methyl, ethyl, n-propyl, cyclopropyl, isopropyl, n-butyl, sec-butyl, isobutyl, 2-methyl butyl, cyclobutyl,

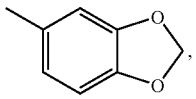

cylcopentyl, allyl, methallyl, CH₂CH(OH)CH₃, CH(CH₃)CH₂OH, CH₂C(CH₃)OH, CH₂CH₂OH, CH₂CO₂CH₃, geranyl, neryl or where R³ and R⁴ together form the structures:

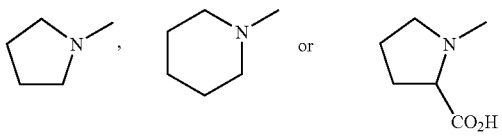

and R⁶ is selected from the group consisting of:
CH₂CH₂CH═CHCH₂CH₃(z);
CH₂CH₂CH═CHCH₂CH₃(z);
CH₂CH═CHCH₂CH₃(z); and
CH₂CH═CHCH₃(z).

3. A process for augmenting, enhancing or imparting an aroma, taste or somatosensory effect to a consumable material selected from the group consisting of a foodstuff, a beverage, a chewing gum, an oral care product, a nasal care product, a cologne, a skin care product, a hair care product, a topical cosmetic product and a medicinal product comprising the step of adding to said consumable material a taste, aroma or somatosensory effect augmenting, enhancing or imparting quantity and concentration of at least one compound of claim 1.

4. A process for augmenting, enhancing or imparting an salty taste to a consumable material selected from the group consisting of a foodstuff, a beverage, a chewing gum, and an oral care product, a topical cosmetic product and a medicinal product comprising the step of adding to said consumable material a taste, aroma or somatosensory effect augmenting, enhancing or imparting quantity and concentration of at least one compound of claim 1.

5. The method of claim 4 wherein the level is greater than about 10 parts per billion.

6. In combination a consumable material selected from the group consisting of foodstuff, a beverage, a chewing gum, and an oral care product, a topical cosmetic product and a medicinal product and the compounds of claim 1.

7. The combination of claim 6 wherein the compound is selected from the group consisting of N-Cyclopropyl 2E,8Z-undecadienamide, N-Ethyl 2E,8Z-undecadienamide and N-(3,4-methylenedioxy) benzyl E2, Z6-nonadienamide.

8. A process for augmenting, enhancing or imparting an aroma, taste or somatosensory effect to a consumable material selected from the group consisting of a foodstuff, a beverage, a chewing gum, an oral care product, a nasal care product, a cologne, a skin care product, a hair care product, a topical cosmetic product and a medicinal product comprising the step of adding to said consumable material a taste, aroma or somatosensory effect augmenting, enhancing or imparting quantity and concentration of at least one compound of claim 2.

9. A process for augmenting, enhancing or imparting an salty taste to a consumable material selected from the group consisting of a foodstuff, a beverage, a chewing gum, and an oral care product, a topical cosmetic product and a medicinal product comprising the step of adding to said consumable material a taste, aroma or somatosensory effect augmenting, enhancing or imparting quantity and concentration of at least one compound of claim 2.

10. The method of claim 9 wherein the level is greater than about 10 parts per billion.

11. In combination a consumable material selected from the group consisting of foodstuff, a beverage, a chewing gum, and an oral care product, a topical cosmetic product and a medicinal product and the compounds of claim 2.

* * * * *